(12) United States Patent
Kelleher et al.

(10) Patent No.: US 7,314,751 B2
(45) Date of Patent: Jan. 1, 2008

(54) FLUORESCENCE DETECTION SYSTEM INCLUDING A PHOTONIC BAND GAP STRUCTURE

(75) Inventors: William P. Kelleher, Action, MA (US); Stephen P. Smith, Medford, MA (US); Richard E. Stoner, Framingham, MA (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 0 days.

(21) Appl. No.: 09/916,419

(22) Filed: Jul. 27, 2001

(65) Prior Publication Data

US 2002/0155592 A1    Oct. 24, 2002

Related U.S. Application Data

(60) Provisional application No. 60/244,279, filed on Oct. 30, 2000.

(51) Int. Cl.
*C12M 1/34* (2006.01)
*G01N 21/64* (2006.01)

(52) U.S. Cl. .............. 435/288.7; 435/287.2; 435/808; 422/82.08; 422/82.11; 385/12

(58) Field of Classification Search ............ 435/288.7, 435/287.2, 287.9, 7.32–7.37, 808; 422/82.05–82.09, 422/82.11; 250/459.1, 461.1, 461.2; 385/12
See application file for complete search history.

(56) References Cited

U.S. PATENT DOCUMENTS

| 4,447,546 A | * | 5/1984 | Hirschfeld .................. 436/527 |
| 5,157,261 A | * | 10/1992 | Grey et al. ............... 250/458.1 |
| 5,250,264 A | * | 10/1993 | Walt et al. ............... 422/82.07 |
| 5,496,700 A | * | 3/1996 | Ligler et al. ................. 435/7.1 |
| 5,690,894 A | * | 11/1997 | Pinkel et al. ............... 422/68.1 |

(Continued)

FOREIGN PATENT DOCUMENTS

EP    1052529 A1    11/2000

(Continued)

OTHER PUBLICATIONS

Cregan, R.F. et al., "Single-Mode Photonic Band Gap Guidance of Light in Air," Science 285, 1537 (1999).

(Continued)

*Primary Examiner*—William H. Beisner
(74) *Attorney, Agent, or Firm*—Mark G. Lappin; Foley & Lardner LLP

(57) ABSTRACT

A fluorescence detection system includes a photonic band gap structure. An internal surface of the photonic band gap structure defines a core region, and is coated with a film formed of conjugated polymer molecules. The core region is filled with a sample fluid or gas having a plurality of either chemical or biological analytes dispersed therein. An optical source generates excitation light directed to the sample fluid. In response, a binding event between a bacterium or chemical species in the fluid or gas and one or more of the conjugated polymer molecules generates a fluorescent signal whose wavelength falls within the photonic band gap. The fluorescent signal is guided through said core region by resonant reflections, and is guided onto a detector. A plurality of photonic band gap structures may be combined so as to form a biosensor array.

22 Claims, 4 Drawing Sheets

U.S. PATENT DOCUMENTS 5,802,236 A   9/1998   DiGiovanni et al.
5,866,430 A   2/1999   Grow

FOREIGN PATENT DOCUMENTS

WO   WO 99/64903   12/1999
WO   WO 00/60388   10/2000

OTHER PUBLICATIONS

Fink, Y. et al., Journal of Lightwave Technology, LT-17, p. 2039-2041 (1999).

Eggleton, B.J. et al., Optics Letters, 24, 1460-1462, Nov. 1, 1999.

* cited by examiner

FLUORESCENCE DETECTION SYSTEM INCLUDING A PHOTONIC BAND GAP STRUCTURE

CROSS-REFERENCE TO RELATED APPLICATIONS

This application claims benefit of priority from U.S. Provisional Patent Application Ser. No. 60/244,279, filed Oct. 30, 2000, entitled HIGH PERFORMANCE BIOLOGICAL DETECTION SYSTEM.

STATEMENT REGARDING FEDERALLY SPONSORED RESEARCH

Not Applicable

REFERENCE TO MICROFICHE APPENDIX

Not Applicable

FIELD OF THE INVENTION

This invention relates generally to a detection system for biochemical agents, and more particularly to a fluorescence detection system that utilizes photonic band gap structures.

BACKGROUND OF THE INVENTION

Fluorescence detection is widely used to detect many types of chemical and biological agents. Typically, fluorescence emission spectra are measured from fluorescence emitting entities, such as microorganisms and chemical compounds, by way of example. Conventional fluorescence detection is very inefficient, however, because in prior art fluorescence detection systems the vast majority of the fluorescence remains uncollected and is wasted.

A prior art fluorescence detection system typically includes a source of fluorescence excitation light, such as a laser, and a sample containing one or more fluorescence emitting agents. The excitation light is directed to the sample, and induces any fluorescence emitting agent present in the sample to fluoresce. An optical detector monitors the fluorescent light emitted by the agent. Typically, a fiber optic waveguide is used to guide the return light from the sample to the sensor. As known in the art, fiber optic waveguides depends on total internal reflections to confine and guide incident light within the fiber optic core.

In prior art fluorescence detection systems, most of the fluorescence does not fall onto the optical detector, and therefore is not collected. When highly sensitive tests are required, this lost fluorescence leads to an undesirable increase in the minimum detectability limits. Also, excitation light and any other background light must be separated from the desired fluorescence signal. In many situations, the signal-to-noise ratio may not be sufficient to prevent the lost signal and the background noise from causing a significant problem.

Further, conventional fiber-optic waveguides require the index of refraction of the cladding to be lower than the index of refraction of the fiber optic core, where the fluorescence takes place. It is very difficult to find structural cladding material with suitable indices of refraction, however, because fluorescence detection of chemical and biological agents is commonly done in a solution. The typical glasses and plastics, from which the claddings of optical fibers are made, have refractive indices that are significantly higher, as compared to the refractive index of aqueous solutions. It is therefore hard to provide a cladding material with suitable indices of refraction, especially when fluorescence detection is performed in an aqueous solution.

While various techniques have been implemented in the prior art to increase the index of the aqueous solution, or to decrease the index of refraction of the confining material, such techniques have only been applicable to a relatively small number of situations. In most situations, the fluorescent molecules were either attached to the outside of the optical fiber core, or were suspended in the cladding of the fiber. In both cases, the collection efficiency of the system is greatly reduced.

It is an object of the present invention to overcome the above-described limitations of prior art fluorescence detection systems. It is another object of the present invention to greatly increase the sensitivity of fluorescence based chemical and biological detectors.

Recently, photonic band gap structures have received a lot of interest from researchers. Unlike optical fibers, photonic band gap structures allow light within certain well-defined wavelength bands to be guided without a total internal reflection mechanism. Photonic band gap structures are configured so as to confine and guide light through resonant reflections, and do not depend on total internal reflections. Accordingly, much greater flexibility is allowed in the design and construction of such structures. For example, the core of a photonic band gap structure is not restricted to materials having a higher index of refraction, as compared to the cladding of the photonic band gap fiber.

It is another object of the present invention to use photonic band gap fibers to significantly increase the sensitivity and selectivity of fluorescence detection systems.

SUMMARY OF THE INVENTION

The present invention provides a high performance fluorescence detection system that uses photonic band gap structures to guide a fluorescent signal from a sample to the detector. The detection sensitivity is enhanced by several orders of magnitude, when compared to prior art fluorescence detection systems that use optical fibers to guide the fluorescent signal from the sample to the detector. In photonic band gap structures, there are no restrictions on the relative indices of refraction of the core and the cladding. Also, a photonic band gap structure can act as an optical filter, so that the signal to noise ratio of the detection system can be enhanced considerably, without using complicated and expensive optical instrumentation. Because the collection efficiency is greatly increased, smaller quantities of samples can be accurately detected.

The present invention features a fluorescence detection system that includes a photonic band gap structure. The photonic band gap structure may be a photonic band gap fiber or a photonic band gap crystal, by way of example. The photonic band gap structure includes an internal surface that defines a core region. In one embodiment, the diameter of the core region is about 14.5 microns. A sample fluid is contained within the core region, and has a plurality of microorganisms, including but not limited to bacteria, dispersed therein. The internal surface of the photonic band gap structure is coated with a film formed of a plurality of conjugate polymer molecules. An optical source generates excitation light directed to the sample fluid. In response to the excitation light, some of the bacteria bind to the conjugated polymer molecules, generating a fluorescent signal.

The photonic band gap structure guides the fluorescence signal through the core region and onto an optical detector, by resonant reflections.

The fluorescent signal is characterized by a wavelength that falls within the band gap of the photonic band gap structure. The fluorescent signal is thus transmitted through the core region and onto the detector by resonant reflections from the photonic band gap structure. The excitation light is characterized by a wavelength that falls outside of the band gap of the photonic band gap structure, and within a transmission band of the photonic band gap structure. In this way, the excitation light is prevented from being guided through the core region onto the detector. Accordingly, the photonic band gap structure acts as a filter for the fluorescence detection system, without the need for complicated and expensive optical instrumentation.

In one embodiment, the collection efficiency of the fluorescence detection system, constructed in accord with the present invention, is about 25%, which represents an improvement of several orders of magnitude, as compared to the prior art. In one embodiment, the signal-to-noise ratio for the fluorescence detection system is about 30.

The present invention also features a detector array for fluorescence detection, formed of an array of photonic band gap fibers. Each photonic band gap fiber includes an internal surface that defines a hollow core region. The internal surface of each photonic band gap fiber is coated with a film formed of conjugated polymer molecules. A sample fluid is contained within each core region of each photonic band gap fiber. A plurality of bacteria are dispersed within the sample fluid. An optical source generates excitation light directed to the sample fluid in each core region. In response to the excitation light, some of the bacteria in the sample fluid in each core region bind with one or more of the conjugated polymer molecules, generating a fluorescent signal. Each photonic band gap fiber guides the fluorescent signal through the core region and onto an optical detector.

DETAILED DESCRIPTION

The present invention relates to a fluorescence detection system which uses photonic band gap structures to guide fluorescent signals. The sensitivity and selectivity of the detection system are significantly increased, as compared to prior art detection systems.

Figures 1A, 1B:
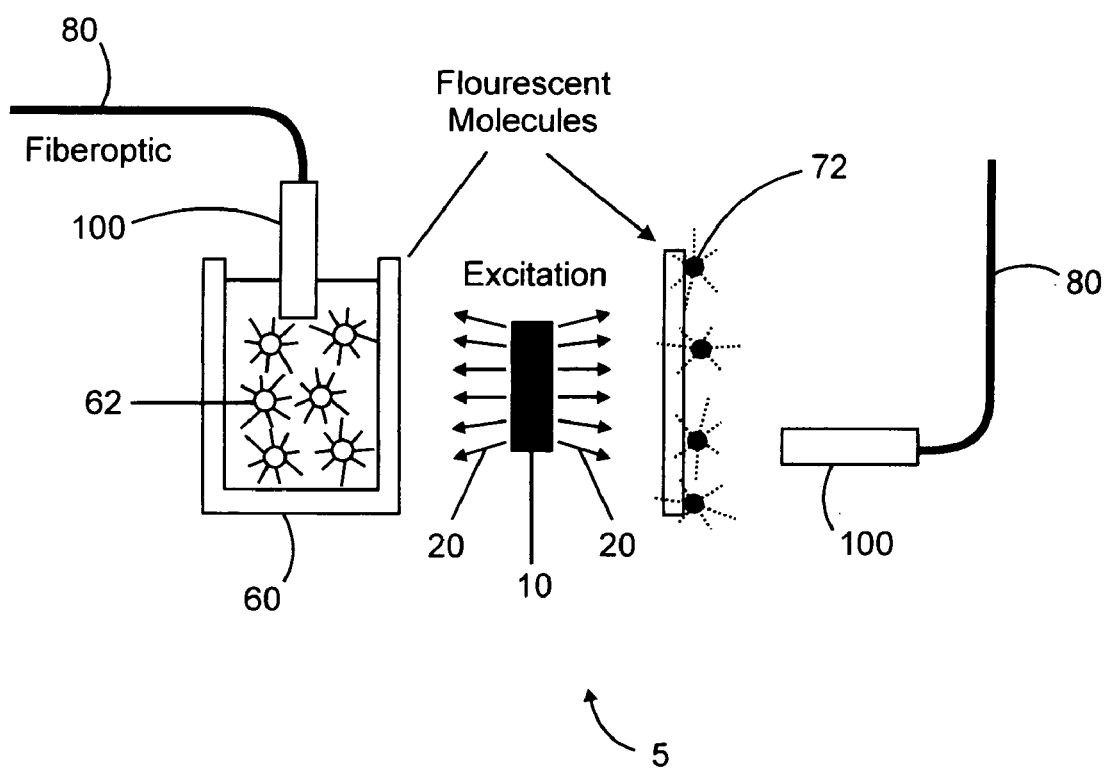
FIGS. 1(a) and 1(b) illustrate a prior art fluorescence detection system that uses fiber optical waveguides.

FIGS. 1(a) and 1(b) illustrate prior art fluorescence detection systems in which fiber optical waveguides are used to guide the light from the sample to the detector. An optical source 10 generates fluorescence excitation light 20, which is directed to samples containing one or more fluorescence emitting agents. Any fluorescence emitting agent present in the sample produces fluorescence emissions, in response to the excitation light 20. In the prior art detection system illustrated in FIG. 1(a), the sample is a solution 60 in which a plurality of fluorescence emitting agents 62 are dispersed. In the prior art fluorescence detection system illustrated in FIG. 1(b), fluorescent emissions are caused by a binding event between fluorescence emitting agents 72 and the molecules that form a surface 70. The surface 70 may be a polymer surface, by way of example.

In both systems, a fiber optic waveguide 80 is used to guide the return light from the sample 30 onto an optical detector 100. The return light includes fluorescent light emitted by the fluorescent emitting agents 62 or 72. As known in the art, optical fibers typically include a core element which has a first refractive index, $n_1$, and a cladding which has a second refractive index, $n_2$. The optical fiber confines light within its core by total internal reflection. Total internal reflection occurs when light is incident upon the barrier between the core element and the cladding at an angle less than a critical angle defined by the difference in the refractive indices of the core element and the cladding, respectively. Total internal reflection thus confines only light that is incident at a limited range of angles. The critical angle $\theta$ is defined by:

$$\theta = \cos^{-1}(n_2/n_1) \quad (1)$$

From equation (1), it can be seen that the core must have a refractive index that is higher than the refractive index of the cladding.

It is difficult, however, to find fiber cladding material having a refractive index that is lower than the refractive index of the core. This is especially true when fluorescence detection takes place in an aqueous solution, as in FIG. 1(a), because the refractive index for aqueous solutions is significantly lower than the refractive index of the claddings of optical fibers, which are typically made of glasses or plastics. It is known that while the index of refraction for aqueous solutions is about 1.33, the refractive index of typical glasses is about 1.5, and the refractive index of typical plastics is about 1.4. Therefore, it is very difficult to procure cladding material that have the refractive index required by equation (1).

For the prior art systems illustrated in FIGS. 1(a) and 1(b), only a small fraction of the fluorescence is collected, typically less than 1%. Prior art fluorescence detection is therefore extremely inefficient. As seen from FIGS. 1(a) and 1(b), in prior art detection systems most of the fluorescent molecules are either attached to the outside of the fiber optical core, or are suspended in the cladding of the optical fiber. Further, absorptive losses are inherent in the use of fiber optical waveguides, since light traveling within a fiber optical core is partially absorbed by the dielectric fiber. To compensate for absorption losses, the fiber may be doped with erbium, which is used to amplify the signal. This limits the bandwidth of the fiber, however, to the narrow bandwidth of the erbium excitation lines. Also, in prior art systems some of the excitation light is collected together with the desired fluorescent signal, reducing the signal-to-noise ratio. An optical filter having a predefined cutoff wavelength is necessary in order to reduce the amount of excitation detected by the optical detector.

In the present invention, photonic band gap structures are used to overcome the above-discussed drawbacks inherent in prior art detection systems, which rely on optical fibers for light propagation. Photonic band gap structures have received widespread interest over the past few years, because they can substantially alter and control the propagation of electromagnetic waves of specific wavelengths.

Photonic band gap structures may be understood by analogy to semiconductor crystals, because photonic band gap structures have the same effect on photons as semiconductor crystals have on electrons. Electronic band structure is a concept well known from solid state physics: due to the periodic potential variations in a crystal, electron motion is restricted, and electrons having a certain energy range are not allowed to travel through the crystal at all. This phenomenon leads to forbidden bands, which form the basis for most microelectronic devices.

Figure 2A:
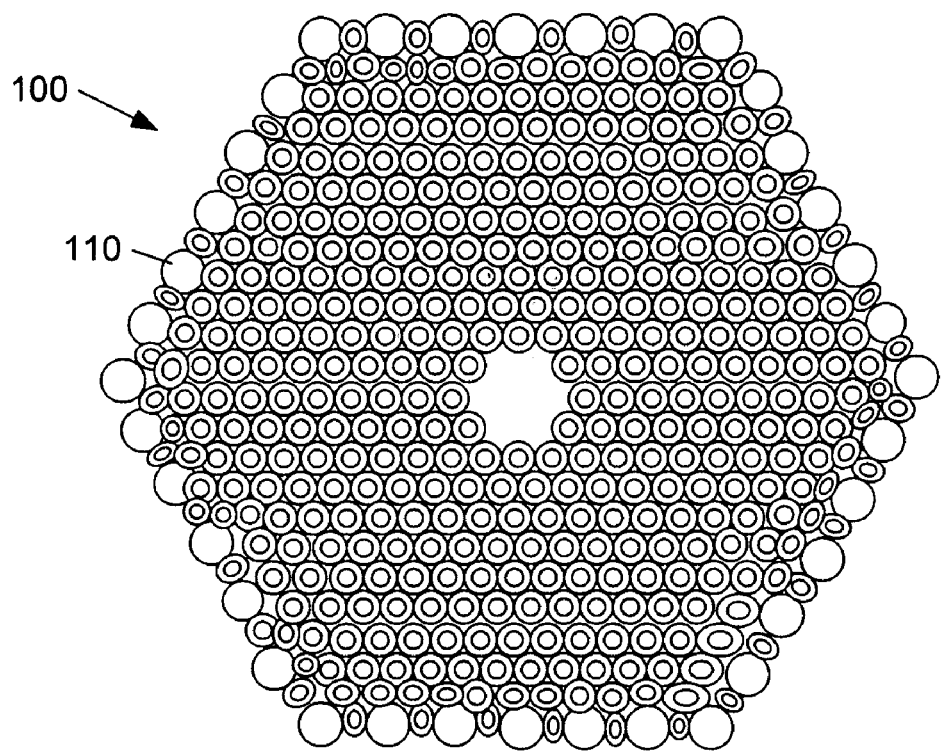
FIGS. 2(a) and 2(b) illustrate a photonic band gap fiber.
Figure 2B:
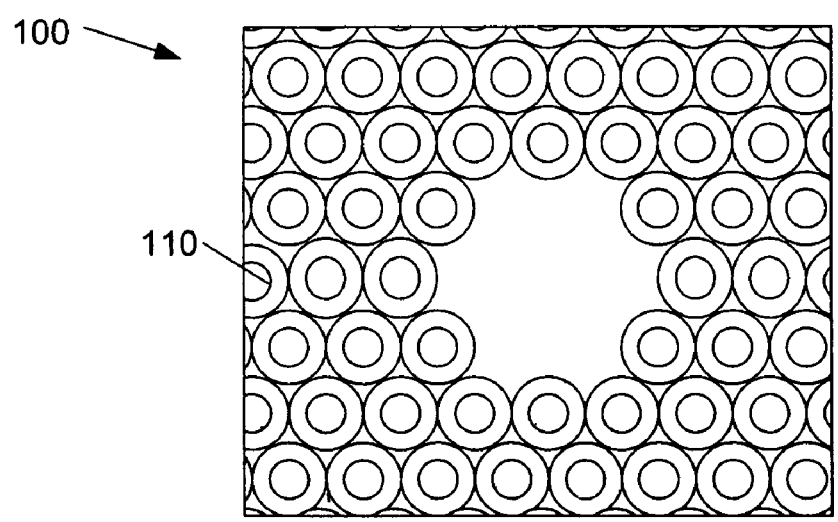

By analogy to lattices in a solid state crystal, a strong periodic variation of the refractive index is created in photonic band gap structures. This variation is on the scale of the wavelength of light. FIGS. 2(a) and 2(b) illustrate a typical photonic band gap structure 100. FIG. 2(b) shows the same structure 100 as if FIG. 2(a), but on an increased magnification level. As seen from FIGS. 2(a) and 2(b), photonic band gap structures consist of a periodic repetition of dielectric elements 110, analogous to the way atoms form a lattice of solid crystals. Light with a wavelength close to the period of the photonic band gap structure 100 will bounce between these elements 110, interfere, and totally reflect back. Light of other colors, i.e. wavelengths, will pass through.

By analogy to electrons in a crystal, photons of electromagnetic radiation propagate through the photonic band gap structure 100, which has a periodically modulated dielectric constant. Electromagnetic radiation that is incident at any angle upon the photonic band gap structure 100 is omnidirectionally reflected by the photonic band gap fiber 100, at certain frequencies of the electromagnetic radiation. This selective filtering is described in terms of a "photonic band gap," i.e. a range of wavelengths of electromagnetic radiation at which propagation through the structure is prohibited, due to interference. The photonic band gap covers a range of frequencies for which any incident electromagnetic wave impinging upon the photonic band gap structure will be reflected, regardless of the angle of incidence. The actual width of the photonic band gap, which may be expressed for example in Hz or in eV, depends upon the geometry, feature size, and spacing of the photonic band gap structure 100, and upon its constituent elements.

Photonic band gap structures may be fabricated by machining blocks of dielectric material, although other methods of fabrication may be known and used. For example, one method of fabricating photonic band gap structures may involve the mechanical drilling or machining of holes or cavities in solid blocks of a dielectric material. Another method may involve the use of chemical removal, such as reactive ion etching, to fabricate holes or cavities in solid blocks of a dielectric material. Alternatively, photonic band gap structures may be fabricated by stacking a collection of dielectric elements in a desired pattern.

In the embodiment illustrated in FIGS. 2(a) and 2(b), the photonic band gap structure 100 was fabricated by stacking a collection of silica rods in a desired pattern, and then reducing the size of the structure by heating and pulling. The photonic band gap structure 100 has a central core, where the light intensity is highest. The central core is approximately 14 microns at its widest, large enough for many bacteria and even many mamallian cells.

In the present invention, the low efficiency collection scheme of prior art fluorescence detection systems is greatly improved by using photonic band gap structures. Since photonic band gap structures confine light by omnidirectional reflections, rather than by total internal reflection as in optical fibers, there are no restrictions on the refractive indices of the core and the cladding, respectively, of the photonic band gap fiber. Therefore, an aqueous core surrounded by a dielectric structure can still guide light within the core. Further, fluorescence in the liquid core is very efficiently confined and guided, since photonic band gap structures are near-perfect reflectors, and are configured to reflect light effectively over all possible angles of incidence.

Figure 3A:
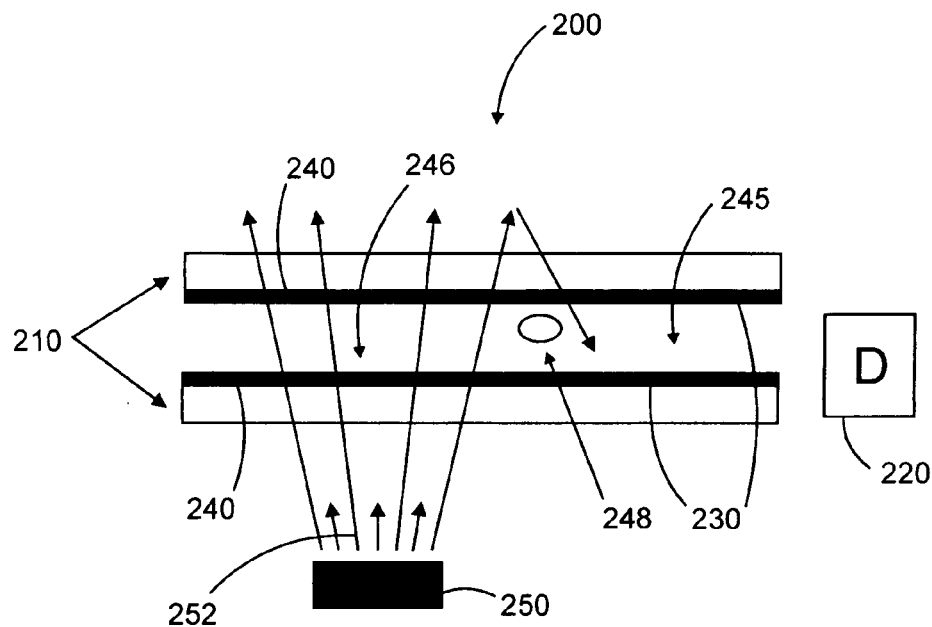
FIGS. 3(a) and 3(b) illustrate a fluorescence detection system that includes a photonic band gap fiber.
Figure 3B:
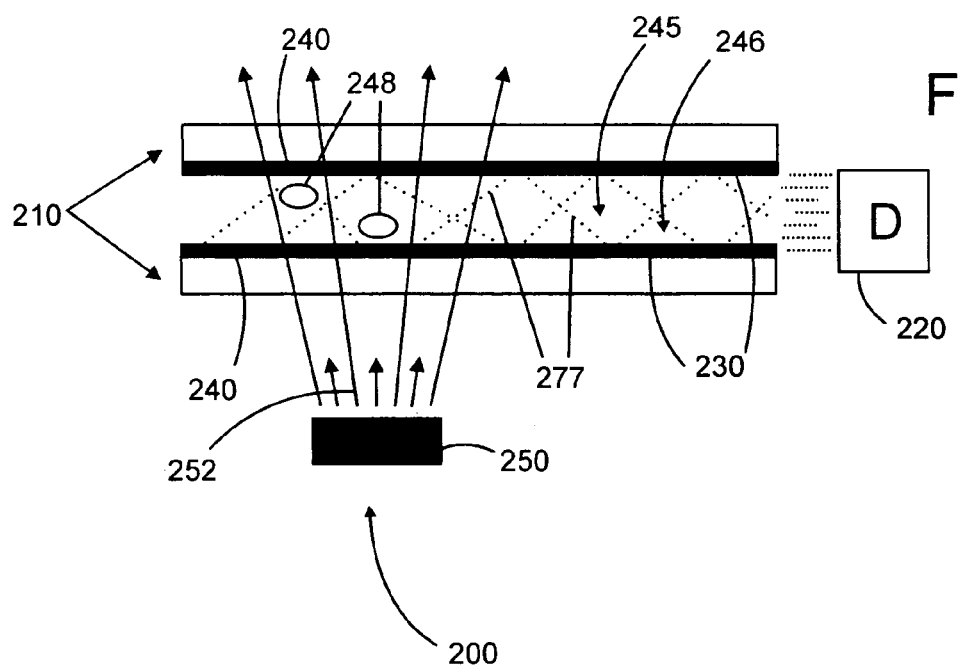

FIGS. 3(a) and 3(b) provide illustrations (not drawn to scale) of a fluorescence detection system 200 constructed in accord with the present invention, in which a photonic band gap structure 210 is used to confine and guide fluorescence light onto an optical detector 220. In the illustrated embodiment, the photonic band gap structure 210 is a photonic band gap fiber. Photonic band gap fibers are small and durable, and can easily be incorporated into small handheld or remote sensors.

In the illustrated embodiment, the photonic band gap fiber 210 includes an internal surface 230 that defines a core region 245. The internal surface 230 is coated with a film 240 that is composed of a plurality of molecules. A sample fluid 246 is contained within the core region 245. A plurality of organisms 248 are dispersed within the sample fluid 246.

An optical source 250 generates excitation light 252 which is directed to the sample fluid 246. In a preferred embodiment, the optical source 250 is a laser. Any laser known in the art may be used, including but not limited to diode lasers, molecular lasers, and solid state lasers. Other sources of high intensity light may be used, including but not limited to flashlamps. In response to the excitation light 252, the organisms 248 within the sample fluid 246 interact with the molecules that form the film 240 so as to generate a fluorescent signal. In a preferred embodiment, the interaction is a binding event. The optical detector 220 detects the fluorescent signal.

In a preferred embodiment, the film 240 is a conjugated polymer biosensing film, formed of conjugated polymer biosensor hybrid molecules. It is advantageous to use conjugated polymer films, because a binding event can cause many of the polymerized sites in a conjugated polymer film to fluoresce. By comparison, in conventional fluorescent systems a binding event causes fluorescence from a single site. In a preferred embodiment of the present invention, a conjugated polymer film 240 is preferably used. In this way, the observed fluorescent signal is greatly amplified. The efficiency of fluorescence collection is thereby further increased.

In an exemplary embodiment, the core region 245 of the photonic band gap fiber 210 is hollow, and contains the sample fluid 246. The core region 245 is very small, so that only very small sample volumes are required. In one embodiment, the diameter of the core region 245 may be of the order of about 14.5 microns. For small test volumes, the fiber 210 may be statically filled with the sample fluid 246, i.e. capillary action may be used to passively fill the fiber 210. Alternatively, the fiber 210 may be used in a flow through mode, where the sample fluid 246 is passed once through the fiber 210, and is then reused or stored.

In the illustrated embodiment, the sample fluid 246 is a liquid, i.e. an aqueous solution. In alternative embodiments, other types of fluids, such as gases, may be used. The plurality of organisms 248 that fill the sample fluid 246 may be biological microorganisms, such as bacteria, antibodies, cells, and proteins. In the embodiment illustrated in FIGS. 3(a) and 3(b), the organism 248 are bacteria. Alternatively, the organisms 248 may be chemical microorganisms, such as inorganic molecules including TNT. In response to the excitation light 252 generated by the optical source 250, the bacteria 248 interact with the molecules forming the film 240, so as to generate a fluorescent signal.

In the embodiment illustrated in FIGS. 3(a) and 3(b), a binding event between the one or more of the bacteria 248 and one or more of the conjugated polymer molecules that form the film 240 induces fluorescence emissions that form a fluorescent signal. The fluorescent signal is guided within the core 240 of the fiber 210 onto the optical detector 220. As illustrated in FIG. 3(a), when no bacteria are bound to the surface 230 of the core region 245, no fluorescent signal is observed. As illustrated in FIG. 3(b), binding of even a few bacteria 248 causes a large fluorescent signal 277, which is guided by the photonic band gap fiber 210 onto the detector 220.

As explained earlier, the photonic band gap fiber 210 is adapted to guide the fluorescent signal through the core region 245 onto the detector by resonant reflections, rather than by total internal reflection. By choosing a photonic band gap fiber 210 having a band gap that encompasses the wavelength of the fluorescent signal 277 being detected, the fluorescent signal 277 can be transmitted through the core region 245 via multiple reflections by the photonic band gap fiber 210. In an exemplary embodiment, the wavelength of the fluorescent light may be from about 400 nm to about 700 nm, although other wavelength ranges are also within the scope of the present invention. In this embodiment, the band gap of the photonic band gap fiber 210 may encompass about a 50 nm wavelength range, which can be detected by the detector 200.

The reflections that the fluorescent signal 277 undergoes while propagating through the core region 245 are near-perfect resonant reflections. As a consequence, the fluorescent signal 277 is omnidirectionally reflected from the fiber 210, without regard to the angle of incidence of the signal. As explained earlier, these resonant reflections are due to the periodic arrangement of the miniature silica rods that make up the fiber 210. The emitted fluorescent signal can therefore be efficiently collected by the photonic band gap fiber 210, and directed onto the optical detector 220.

Because of the resonant nature of the photonic band gap fiber 210, the fiber 210 can act as an optical filter for the excitation light 252. In a preferred embodiment, the excitation light 252 is chosen to be characterized by a wavelength that falls outside of the band gap of the fiber 210 and within a transmission band of the fiber 210. In this way, the excitation light 252 is prevented from being guided through the core region 245 through multiple reflections. Rather, the excitation light 252 passes straight through the fiber 210, and does not fall onto the detector 220.

In the embodiment illustrated in FIGS. 3(a) and 3(b), the collection efficiency for the fluorescence detection system 200 is about 25%, depending on the exact parameters of the photonic band gap fiber 210. By comparison, the prior art fluorescence detection systems illustrated in FIGS. 1(a) and 1(b) have a collection efficiency that is considerably less than 1%. The present invention therefore achieves an improvement in collection efficiency of several orders of magnitude, as compared to the prior art.

Since the excitation wavelength is not guided onto the detector, the signal-to-noise ratio for the fluorescence detection system 200 is also significantly increased. In one embodiment, the signal-to-noise ratio is about 30. Because no separate optical filter is required in order to separate out the excitation light 252 and other noise from the desired fluorescent signal, the instrumentation for the detection system 200 is considerably simplified.

Figure 4A:
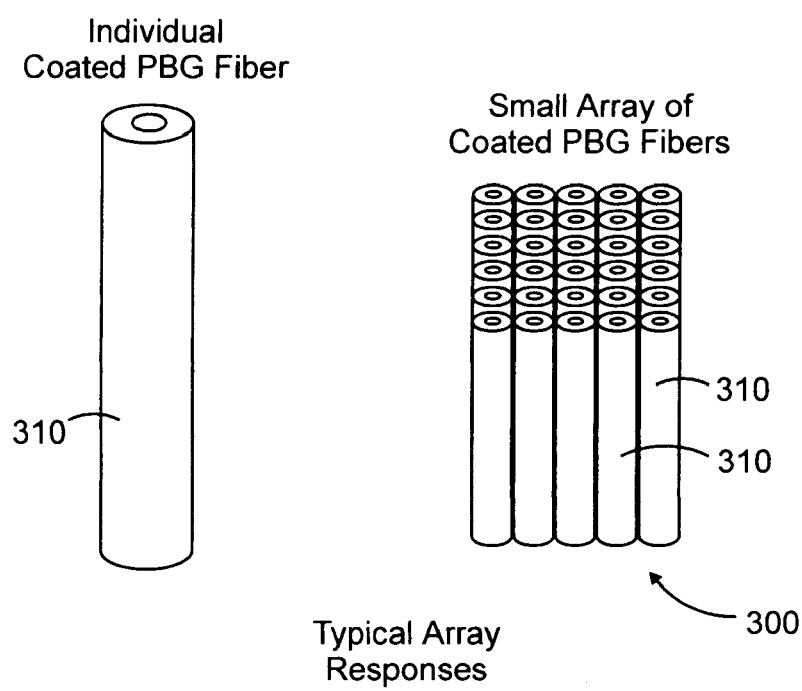
FIG. 4 is a schematic diagram of a fluorescence detection system formed of an array of photonic band gap fibers.

The technique of the present invention, described in conjunction with FIGS. 3(a) and 3(b), can easily be scaled to make detector arrays. FIG. 4(a) is a schematic diagram of a fluorescence detection system that includes an array 300 of photonic band gap fibers 310. In the embodiment illustrated in FIG. 4(a), the array 300 includes a plurality of photonic band gap fibers 310, each of which has an internal surface that is coated with a conjugated polymer film. In one embodiment, different conjugated polymer films may be used for different photonic band gap fibers. After being coated with a conjugate polymer film at the respective internal surfaces, the photonic band gap fibers may be combined into a bundle, similar to an optical fiber. The bundle can be used as a simple, portable biosensor. The array 300 can be filled with a sample fluid via capillary action.

Figure 4B:
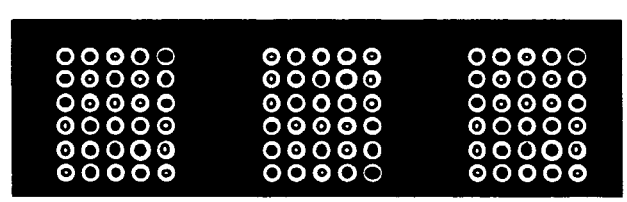

FIG. 4(b) provides an illustration of typical array responses, as detected by the array 300. By appropriately arranging the coated fibers 310, the readout from the array 300 can be simplified. By way of example, the array output can use both color (e.g. red—anthrax, blue—botulinum, green—cholera, etc.) and patterns to provide a readout that can easily be interpreted even by untrained personnel.

The present invention provides a high performance biological or chemical detection system that combines a state of the art development in physics, namely photonic band gap structures, with a very successful, state of the art detection chemistry, namely conjugated polymer biosensor films. The result is a fluorescent detection system having a greatly enhanced sensitivity and selectivity, as compared to the prior art. Because of the greatly enhanced collection efficiency, the present invention allows for smaller quantities of materials to be accurately detected, as compared to the prior art.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A fluorescence detection system for detecting predetermined materials in a sample fluid, comprising:
   A. a photonic band gap structure characterized by a photonic band gap, and including an internal surface that defines a core region; wherein said internal surface of said photonic band gap structure is coated with a film formed of a plurality of molecules, said core region being adapted to receive a sample fluid therein;
   B. an optical source for generating excitation light characterized by a wavelength outside said photonic band gap and directed to said core region; wherein said predetermined material is capable of interacting with at least one of said plurality of molecules whereby upon such interaction and in response to said excitation light, said at least one of said conjugated polymer molecules generates a fluorescent signal; and
   C. an optical detector for detecting said fluorescence signal; wherein said photonic band gap structure is adapted to guide said fluorescence signal through said core region and onto said detector for detection by said detector.

2. A fluorescence detection system according to claim 1, wherein said predetermined material interacts with said at least one of said conjugated polymer molecules through a binding event.

3. A fluorescence detection system according to claim 1, wherein said fluorescence signal comprises fluorescence emissions from a plurality of said conjugated polymer molecules.

4. A fluorescence detection system according to claim 1, wherein the collection efficiency of said fluorescence detection system is about 25%.

5. A fluorescence detection system according to claim 1, wherein the signal-to-noise ratio for said fluorescence detection system is about 30.

6. A fluorescence detection system according to claim 1, wherein said optical source is a laser.

7. A fluorescence detection system according to claim 1, wherein said predetermined material is selected from the group consisting of bacteria, antibodies, cells, and proteins.

8. A fluorescence detection system according to claim 1, wherein said optical detector is a photomultiplier.

9. A fluorescence detection system according to claim 1, wherein a volume of said fluid is less than about one microliter.

10. A fluorescence detection system according to claim 1, wherein a diameter of said core region is about 14.5 microns.

11. A fluorescence detection system according to claim 1, wherein said predetermined material may comprise at least one of a biological microorganism and/or a chemical.

12. A fluorescence detection system according to claim 11, wherein said chemical is TNT.

13. A fluorescence detection system according to claim 1, wherein said sample fluid comprises a liquid.

14. A fluorescence detection system according to claim 1, wherein said sample fluid comprises a gas.

15. A fluorescence detection system according to claim 4, wherein said wavelength of said fluorescent light is from about 400 nm to about 700 nm.

16. A fluorescence detection system according to claim 1, wherein said photonic band gap structure is selected from the group consisting of a photonic band gap fiber and a photonic band gap crystal.

17. A fluorescence detection system according to claim 1, wherein said photonic band gap structure is configured so that said core region is adapted to be filled with said fluid via a capillary action.

18. A fluorescence detection system according to claim 1 wherein said photonic band gap structure is tubular along an axis wherein said core region extends along said axis, and wherein said optical detector is disposed along said axis.

19. A detector array for fluorescence detection of predetermined materials in a sample fluid, said detector array comprising:

A. an array of photonic band gap fibers each of said photon band gap fibers being characterized by a photonic band gap, and each photonic band gap fiber including an internal surface that defines a hollow core region; wherein each internal surface of each photonic band gap fiber is coated with a film formed of a plurality of conjugated polymer molecules, and wherein said core regions are adapted to receive a sample fluid; and B. an optical source for generating excitation light characterized by a wavelength outside said photonic band gap, and directed to said core regions; wherein said predetermined material is capable of binding with at least one of said plurality of conjugated polymer molecules and upon such binding of one of said plurality of conjugated polymer molecules, said one conjugated polymer molecule is responsive to said excitation light so as to generate a fluorescence signal characterized by a wavelength within said photonic band gap; and C. a detector for detecting said fluorescence signal; wherein each photonic band gap fiber is adapted to guide said fluorescence signal through said core region and onto said detector for detection by said detector.

20. A detector array according to claim 19 wherein said core regions of said fibers extend along substantially parallel axes and wherein said detector is disposed along said axes.

21. A detector array according to claim 20 wherein said optical source directs said excitation light to said core regions at least in part transverse to said axes.

22. A fluorescence detection system according to claim 18 wherein said optical source directs said excitation light to said core region at least in part transverse to said axis.

* * * * *

UNITED STATES PATENT AND TRADEMARK OFFICE
CERTIFICATE OF CORRECTION

PATENT NO. : 7,314,751 B2  Page 1 of 1
APPLICATION NO. : 09/916419
DATED : January 1, 2008
INVENTOR(S) : William P. Kelleher, Stephen P. Smith and Richard E. Stoner It is certified that error appears in the above-identified patent and that said Letters Patent is hereby corrected as shown below:

1. At Column 8, Line 41, should read as follows:
-- formed of a plurality of conjugated polymer molecules, said core region --

2. At Column 9, Line 25, should read as follows:
-- A fluorescence detection system according to claim 1, --

Signed and Sealed this

First Day of July, 2008

JON W. DUDAS
*Director of the United States Patent and Trademark Office*